US009308090B2

(12) United States Patent
Thorwarth et al.

(10) Patent No.: US 9,308,090 B2
(45) Date of Patent: Apr. 12, 2016

(54) COATING FOR A TITANIUM ALLOY SUBSTRATE (71) Applicants: Kerstin Thorwarth, Dubendorf (CH); Roland Hauert, Suhr (CH); Gotz Thorwarth, Dubendorf (CH)

(72) Inventors: Kerstin Thorwarth, Dubendorf (CH); Roland Hauert, Suhr (CH); Gotz Thorwarth, Dubendorf (CH)

(73) Assignee: DePuy Synthes Products, Inc., Raynham, MA (US)

(*) Notice: Subject to any disclaimer, the term of this patent is extended or adjusted under 35 U.S.C. 154(b) by 0 days.

(21) Appl. No.: 13/793,470

(22) Filed: Mar. 11, 2013

(65) Prior Publication Data
US 2014/0257494 A1 Sep. 11, 2014

(51) Int. Cl.
B32B 9/00 (2006.01)
A61F 2/30 (2006.01)
A61L 27/04 (2006.01)
A61L 27/06 (2006.01)
A61L 27/30 (2006.01)

(52) U.S. Cl.
CPC ............... *A61F 2/30* (2013.01); *A61L 27/045* (2013.01); *A61L 27/06* (2013.01); *A61L 27/303* (2013.01); *A61L 2420/02* (2013.01); *A61L 2420/08* (2013.01)

(58) Field of Classification Search
None
See application file for complete search history.

(56) References Cited

U.S. PATENT DOCUMENTS

| 5,799,549 | A | 9/1998 | Decker et al. |
| 6,740,393 | B1 | 5/2004 | Massler |
| 7,800,285 | B2 | 9/2010 | Andle et al. |
| 9,169,551 | B2 | 10/2015 | Hauert et al. |
| 9,175,386 | B2 | 11/2015 | Hauert et al. |
| 2003/0104028 | A1 | 6/2003 | Hossainy et al. |
| 2004/0220667 | A1 | 11/2004 | Gelfandbein et al. |
| 2005/0100578 | A1 | 5/2005 | Schmid et al. |
| 2006/0040105 | A1 | 2/2006 | Sato et al. |
| 2008/0103597 | A1 | 5/2008 | Lechmann et al. |
| 2008/0154369 | A1* | 6/2008 | Barr et al. .................. 623/11.11 |
| 2010/0247885 | A1 | 9/2010 | Ito et al. |
| 2011/0307068 | A1* | 12/2011 | Hauert et al. ............... 623/23.6 |

(Continued)

FOREIGN PATENT DOCUMENTS

WO 00/75394 12/2000
WO 2007/109714 9/2007

(Continued)

OTHER PUBLICATIONS

The International Search Report for International Patent Application No. PCT/US2014/018890, dated Jul. 17, 2014, 4 pages.

(Continued)

*Primary Examiner* — Daniel J Schleis
(74) *Attorney, Agent, or Firm* — Morgan Lewis Bockius, LLP (57) ABSTRACT The present disclosure relates, at least in part, to a surgical implant and a method for manufacturing the surgical implant. In one embodiment, the surgical implant comprises a metallic substrate; a tantalum interlayer disposed adjacent to the metallic substrate and comprising α-tantalum and amorphous tantalum; at least one DLC layer disposed adjacent the tantalum interlayer; wherein the amorphous tantalum has a phase gradient increasing from the metallic substrate side to the DLC side; wherein the DLC layer has a hardness value and an elastic modulus value; and wherein the hardness value has a gradient increasing away from the tantalum side; and wherein the elastic modulus value has a gradient from the tantalum side.

14 Claims, 6 Drawing Sheets (56) References Cited

U.S. PATENT DOCUMENTS

2011/0320006 A1* 12/2011 Voisard et al. ............. 623/23.53
2013/0060340 A1 3/2013 Hauert et al.

FOREIGN PATENT DOCUMENTS

WO 2007/123539 11/2007
WO 2014163919 10/2014

OTHER PUBLICATIONS

The Written Opinion for International Patent Application No. PCT/US2014/018890, dated Jul. 17, 2014, 5 pages.

Kiuru, M. et al. "Tantalum as a Buffer Layer in Diamond-Like Carbon Coated Artificial Hip Joints", Journal of Biomedical Materials Research Part B: Applied Biomaterials, vol. 66, 2003, pp. 425-428.

Tiainen, V-M. "Amorphous carbon as a bio-mechanical coating—mechanical properties and biological applications", Diamond and Related Materials, vol. 10, 2001, pp. 153-160.

Santavirta, S. et al. "Some relevant issues related to the use of amorphous diamond coatings for medical applications", Diamond and Related Materials, vol. 7, 1998, pp. 482-485.

Taeger, G. et al. "Comparison of Diamond-Like-Carbon and Alumina-Oxide articulating with Polyethylene in Total Hip Arthroplasty." Mat.-wiss. u. Werkstofftech. 2003, vol. 34, No. 12, pp. 1094-1100.

S.L. Lee et al., "High-rate Sputter Deposited tantalum Coating on Steel for Wear and Erosion Mitigation", Jul. 6, 2001, Surface and Coatings Technology 149 (2002) 62-69, Elsevier, U.S.

Alakoski, Esa, Mirjami Kiuru, Veli-Matti Tiainen, Asko Anttila, "Adhesion and quality test for tetrahedral amorphous carbon coating process," Diamond and Related Materials, vol. 12, Issue 12, Dec. 2003, pp. 2115-2118.

* cited by examiner

COATING FOR A TITANIUM ALLOY SUBSTRATE

BACKGROUND OF THE INVENTION

Figure 1A:
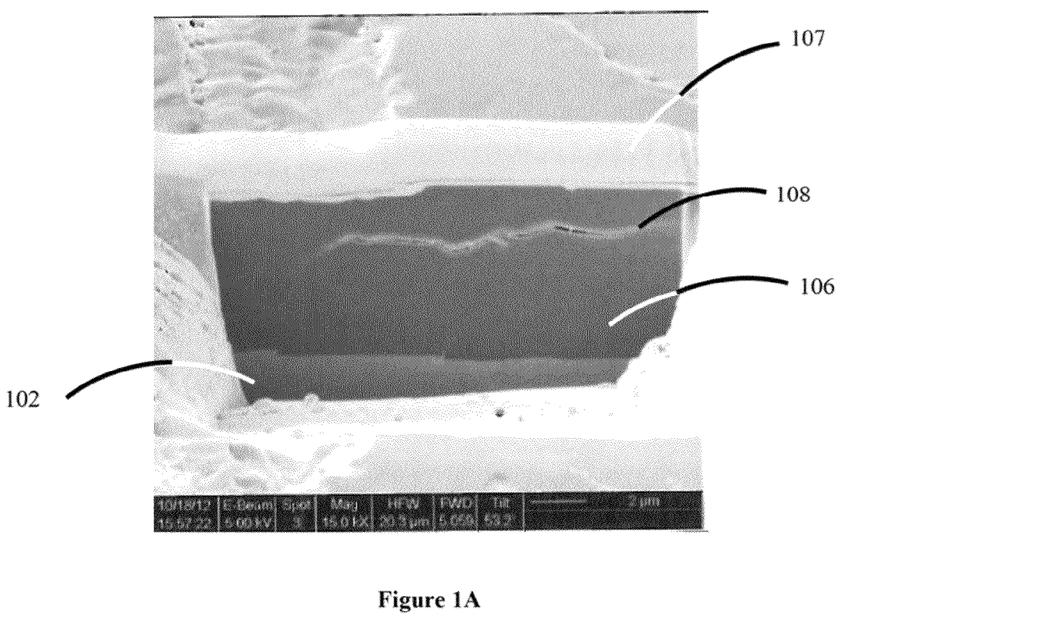
FIG. 1A is a scanning electron microscopy (SEM) image of a non-graded tantalum and DLC lubricant coating deposited on TiAl6Nb7.
Figure 1B:
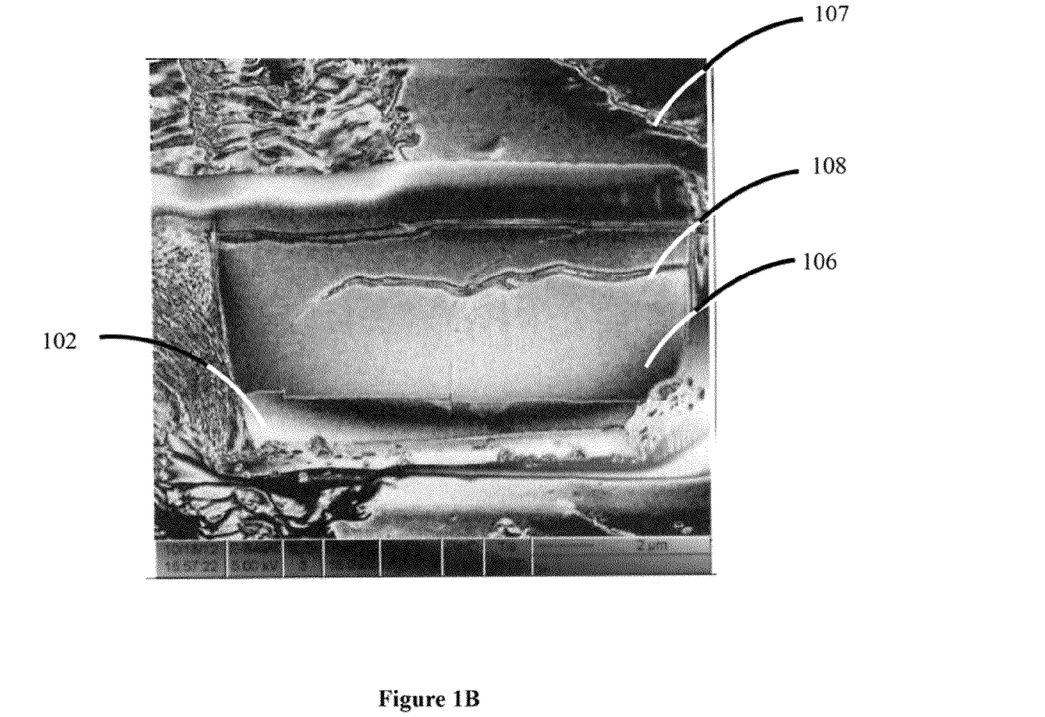
FIG. 1B is a scanning electron microscopy (SEM) image of a non-graded tantalum and DLC lubricant coating deposited on TiAl6Nb7.

Due to its unique combination of hardness, wear resistance, low deposition temperature (below 150° C.), biocompatibility, and friction characteristics (friction coefficient below 0.1), DLC is ideally suited for applications in a variety of fields, including tribology, corrosion protection, and medical devices. However, in applications of DLC as hard coatings, the high residual stresses associated with its deposition gives rise to poor adhesion strength, brittle fracture and delamination under high local loading. Referring to FIG. 1A, for example, there is shown a secondary electron microscopy ("SEM") image of a cross section of ungraded DLC coating 106 deposited on a Titanium-Aluminum-Niobium (Ti6Al7Nb) substrate 102. As shown in FIG. 1, the ungraded DLC coating 106 exhibited poor tolerance for deformations underneath it ("eggshell effect"), and due to its brittleness and low elongation at failure developed cracks 108. Layer 107 is a platinum coating used to enhance conductivity around the ungraded DLC coating 106 deposited on a Titanium-Aluminum-Niobium (Ti6Al7Nb) substrate 102. FIG. 1B illustrates a contrast adjusted SEM image shown in FIG. 1A, which better shows the cracks in the DLC coating. The cracks 108 compromise the integrity of the DLC coating 106 and lead to failure of the DLC coated Ti6Al7Nb substrate 102 (e.g., delaminated prosthesis) by generating hard wear debris. Accordingly, a need exists for more robust coated metal-based prostheses that are able exhibit high tolerance for both elastic and plastic deformations, and therefore prevent development of cracks that compromise the integrity of the coating and the coated prostheses.

BRIEF SUMMARY OF THE INVENTION

In one aspect, the present invention provides for a surgical implant. In one embodiment, the surgical implant comprises a metallic substrate. In one embodiment, there is a tantalum interlayer disposed adjacent to the metallic substrate. In one embodiment, the tantalum interlayer comprises α-tantalum and amorphous tantalum. In one embodiment, the surgical implant includes at least one DLC layer disposed adjacent the tantalum interlayer. In one embodiment, the tantalum interlayer has a phase gradient between the metallic substrate side and the DLC side. In one embodiment, the tantalum interlayer has a phase gradient from β-tantalum to α-tantalum between the metallic substrate side and the DLC side. In one embodiment, the amorphous tantalum of the tantalum interlayer has a crystallinity gradient increasing from the metallic substrate side to the DLC side. In one embodiment, the DLC layer has a hardness value and an elastic modulus value. In one embodiment, the hardness value of the DLC layer has a gradient increasing away from the tantalum side. In one embodiment, the elastic modulus value of the DLC layer has a gradient increasing away from the tantalum side.

In some embodiments, the metallic substrate of the surgical implant independently includes titanium, a titanium based alloy, a cobalt based alloy or steel. In some embodiments, the tantalum interlayer of the surgical implant has a thickness ranging from 1 nm to 2 µm.

In some embodiments, the tantalum interlayer independently further comprises an element or compound, wherein the element or compound promotes the growth of α-tantalum. In some such embodiments, the element independently includes titanium, niobium, tungsten and combinations thereof. In other such embodiments, the compound independently includes titanium compound, niobium compound, tungsten compound or combinations thereof.

In some embodiments, the tantalum interlayer of the surgical implant further comprises tantalum compound nanoparticles. In some embodiments, the tantalum interlayer of the surgical implant is a nanocomposite of tantalum-carbide and tantalum. In some embodiments, the surgical implant has a DLC layer with a hardness value gradient that increases from 12 GPa to 22 GPa. In some embodiments, the surgical implant has a DLC layer with an elastic modulus value gradient that increases from 120 GPa to 220 GPa. In some embodiments, the surgical implant has at least one DLC layer comprising a plurality of alternating sub-layers. In one embodiment, the plurality of alternating sub-layers comprises a DLC sub-layer and a doped DLC sub-layer. In one embodiment, the doped DLC sub-layer is doped with a metal. In one embodiment, the metal doped DLC sub-layer is doped with titanium.

In another aspect, the present invention provides for a method for manufacturing an exemplary surgical implant in accordance with present invention. In one embodiment, the method comprises inserting a metallic substrate into a vacuum system. In one embodiment, the method includes cleaning the metallic substrate by Ar+ bombardment at a RF self bias ranging from about −200 volts to about −2000 volts. In one embodiment, the metallic substrate is cleaned by Ar+ bombardment at a RF self bias of −600 volts.

In one embodiment, the method includes depositing a tantalum interlayer while applying an electrical bias to the substrate. In one embodiment, the bias is a RF self bias. In one embodiment, the applied RF self bias ranges from −50 volts to −600 volts. In one embodiment, the applied RF self bias is changed in predetermined increments. In one embodiment, the applied RF self bias is changed in stepwise increment ranging from a 5 volt step to a 50 volt step.

In one embodiment, the method includes depositing a DLC layer. In one embodiment, the DLC layer is deposited by introducing a hydrocarbon at a second specified RF self bias to the substrate. In one embodiment, the DLC layer is deposited by introducing a hydrocarbon at the second RF self bias that is changed from −50 volts to −600 volts in a stepwise increment. In one embodiment, the applied second RF self bias is changed in stepwise increment ranging from a 5 volt step to a 50 volt step. In one embodiment, the DLC layer is deposited by introducing a hydrocarbon having a molecular weight ranging from 92 g/mole to 120 g/mole. In one embodiment, the DLC layer is deposited by introducing a hydrocarbon independently selected from the group consisting of toluene, xylene, trimethyl benzene, and combinations thereof.

In some embodiments, the method for manufacturing a surgical implant according to the present invention includes the step of introducing an acetylene atmosphere at a third RF self bias to the substrate. In one embodiment, the applied third RF self bias is changed from −50 volts to −600 volts in a second stepwise increment. In one embodiment, the second stepwise increment ranges from a 5 volt step to a 50 volt step.

In another embodiment, a method for manufacturing a surgical implant, in accordance with the present invention, includes the steps of: (a) inserting a metallic substrate into a vacuum system; (b) cleaning the metallic substrate by Ar⁺ bombardment at a RF self bias to the substrate ranging from about −200 volts to about −2000 volts, preferably at a RF self bias of −600 volts; (c) depositing a tantalum interlayer by applying an electrical bias, including a RF self bias, to the substrate during tantalum deposition, said RF self bias ranging from −50 volts to −600 volts; (d) depositing a DLC layer by introducing an acetylene atmosphere at a RF self bias, wherein the RF self bias is changed from −50 volts to −600 volts in a stepwise increment for a first time period; (e) after the first time period, introducing a organotitanium source into the acetylene atmosphere for a second time period; and (f) repeating steps (d) and (e) up to one hundred repetitions. In one embodiment, the stepwise increment ranges from a 5 volt step to a 50 volt step.

BRIEF DESCRIPTION OF THE SEVERAL VIEWS OF THE DRAWINGS

The foregoing summary, as well as the following detailed description of embodiments of the surgical implant and method of manufacturing the same, will be better understood when read in conjunction with the appended drawings of an exemplary embodiment. It should be understood, however, that the invention is not limited to the precise arrangements and instrumentalities shown.

In the drawings.

DETAILED DESCRIPTION OF THE INVENTION

Referring to the drawings in detail, wherein like reference numerals indicate like elements throughout, there is shown in FIGS. 2-6 a schematic cross-section view of a coated surgical implant generally designated with reference numeral 100, in accordance with exemplary embodiments of the present invention.

The present invention generally relates to prosthetic orthopedic implants, particularly to joint components such as for use with knees, hips, shoulders, elbows, toes, fingers, wrists, ankles and spinal disc replacements. More specifically, the present invention relates to a method of making a non-modular prosthetic joint component having a metal substrate, tantalum interlayer, and DLC layer.

Figure 2:
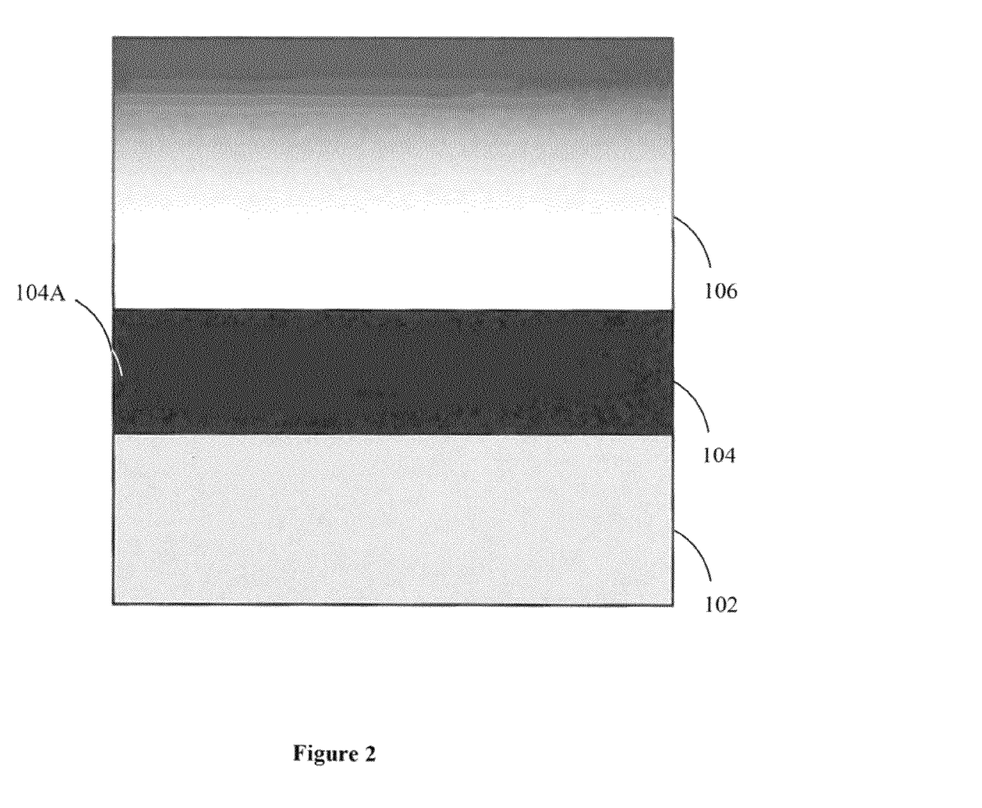
FIG. 2 is a schematic cross-section view of a coated surgical implant in accordance with an exemplary embodiment of the present invention.

In an aspect, the present invention provides a surgical implant having a metallic substrate coated with at least one layer comprising DLC. As shown in FIG. 2, in one embodiment, surgical implant 100 comprises a metallic substrate 102 have a coating that includes a tantalum interlayer 104 disposed adjacent to metallic substrate 102. In one embodiment, surgical implant 100 includes metallic substrate 100 and tantalum interlayer 104 comprising α-tantalum. In one embodiment, surgical implant 100 includes metallic substrate 102 and tantalum interlayer 104 comprising amorphous tantalum. In one embodiment, surgical implant 100 includes metallic substrate 102 and tantalum interlayer 104 comprising α-tantalum and amorphous tantalum. In one embodiment, surgical implant 100 includes metallic substrate 102 and at least one DLC layer 106 disposed adjacent tantalum interlayer 104. In one embodiment, the tantalum interlayer has a phase gradient between the metallic substrate side and the DLC side. In one embodiment, surgical implant 100 includes metallic substrate 102 and tantalum interlayer 104 comprising an amorphous tantalum having a crystallinity gradient. In one embodiment, surgical implant 100 includes metallic substrate 102 and tantalum interlayer 104 comprising an amorphous tantalum having a crystallinity gradient that increases from metallic substrate 102 side to DLC layer 106 side. In one embodiment, surgical implant 100 includes tantalum interlayer 104 having a phase gradient from β-tantalum to α-tantalum.

In one embodiment, surgical implant 100 includes metallic substrate 102, tantalum interlayer 104 and DLC layer 106 having a hardness value and an elastic modulus value. In one embodiment, surgical implant 100 includes metallic substrate 102, tantalum interlayer 104 and DLC layer 106 having a hardness value and an elastic modulus value, wherein the hardness value has a gradient increasing away from tantalum interlayer 104 side. In one embodiment, surgical implant 100 includes metallic substrate 102, tantalum interlayer 104 and DLC layer 106 having a hardness value and an elastic modulus value, wherein the elastic modulus value has a gradient increasing away from the tantalum interlayer 104 side.

In one embodiment, surgical implant 100 includes metallic substrate 102; tantalum interlayer 104 disposed adjacent to metallic substrate 100 and comprising α-tantalum and amorphous tantalum; at least one DLC layer 106 disposed adjacent tantalum interlayer 104. In one embodiment, surgical implant 100 includes metallic substrate 102; tantalum interlayer 104 disposed adjacent to metallic substrate 102 and comprising α-tantalum and amorphous tantalum; and at least one DLC layer 106 disposed adjacent tantalum interlayer 104, wherein the amorphous tantalum has a concentration gradient increasing from metallic substrate 100 side to the DLC layer 106 side. In one embodiment, surgical implant 100 includes metallic substrate 102; tantalum interlayer 104 disposed adjacent to metallic substrate 102 and comprising α-tantalum and amorphous tantalum; and at least one DLC layer 106 disposed adjacent tantalum interlayer 104, wherein DLC layer 106 has a hardness value and an elastic modulus value; and wherein the hardness value has a gradient increasing away from tantalum interlayer 104 side. In one embodiment, surgical implant 100 includes metallic substrate 102; tantalum interlayer 104 disposed adjacent to metallic substrate 102 and comprising α-tantalum and amorphous tantalum; and at least one DLC layer 106 disposed adjacent tantalum interlayer 104, wherein the elastic modulus value has a gradient increasing away from tantalum interlayer 104 side.

Metallic substrate 102 of surgical implant 100 in accordance with exemplary embodiments of the present invention can comprise any suitable metal, metal alloy or a combination of both. Generally, metallic substrate 102 can include any metals and metal alloys that possess any advantageous combinations of properties, thermal and mechanical characteristics, including little heating and high levels of endurance strength during alternating repetition of loads. In one embodiment, metallic substrate 102 comprises a titanium-based alloy. In one embodiment, metallic substrate 102 comprises a titanium-based alloy selected from the group consisting of TiAl6V4, TiAl6Nb7 and a combination thereof. In one embodiment, metallic substrate 102 comprises a cobalt-chromium (CoCrMo) alloy. In one embodiment, metallic substrate 102 comprises steel. In one embodiment, metallic substrate 102 comprises at least one element selected from the group consisting of titanium, nickel, iron, cobalt, niobium, zinc, tungsten, molybdenum, and tantalum. In one embodiment, metallic substrate 102 comprises a metal alloy in which at least one of the elements is selected from the group consisting of titanium, nickel, iron, cobalt, niobium, zinc, tungsten, molybdenum, and tantalum. In one embodiment, metallic substrate 102 comprises titanium and/or a titanium alloy selected from the group consisting of unalloyed commercially pure (CP) titanium, TiAl6V4, TiAl6Nb7, or nickel-titanium (superelastic NiTi or shape-memory NiTi).

In some exemplary embodiments, metallic substrate 102 of surgical implant 100 in accordance with the present invention preferably comprises a titanium alloy. Benefits of using titanium alloys as prosthesis materials include high mechanical load-bearing capacity, high fatigue strength, elasticity, high chemical stability, improved magnetic resonance imaging ("MRI") and computed tomography ("CT") compatibility, and superior biocompatibility. Also, many different types of surgical implants, including bone plates, pins, artificial knee and hip joints, and intervertebral disk prostheses can be advantageously fabricated from titanium-based alloys. However, titanium based alloys exhibit inadequate wear behavior in articulation in addition to difficult finishing capabilities, requiring a wear-resistant coating.

Figure 3:
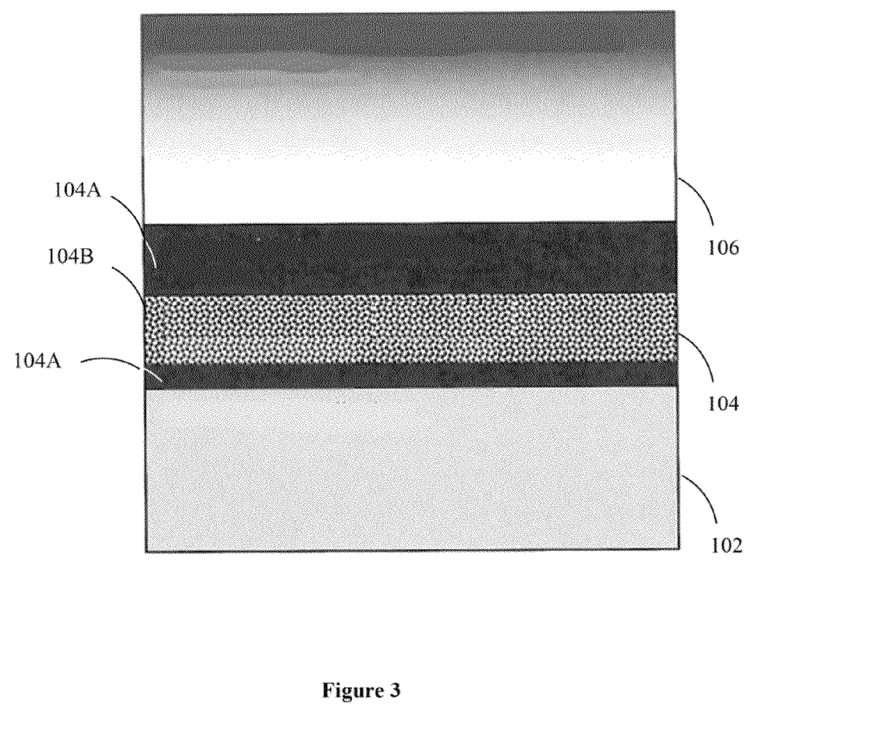
FIG. 3 is a schematic cross-section view of a graded DLC lubricant coating deposited on a surgical implant in accordance with an exemplary embodiment of the present invention.

Referring to FIGS. 2 and 3, tantalum interlayer 104 in accordance with an exemplary embodiment of the present invention is preferably disposed adjacent to metallic substrate 102. In one embodiment, tantalum interlayer 104 comprises crystalline tantalum. In one embodiment, tantalum interlayer 104 comprises crystalline tantalum and amorphous tantalum. In one embodiment, tantalum interlayer 104 comprises α-tantalum. In one embodiment, tantalum interlayer 104 comprises β-tantalum and α-tantalum. In one embodiment, tantalum interlayer 104 comprises β-tantalum and amorphous tantalum. In one embodiment, tantalum interlayer 104 comprises β-tantalum, α-tantalum and amorphous tantalum.

Figure 5:
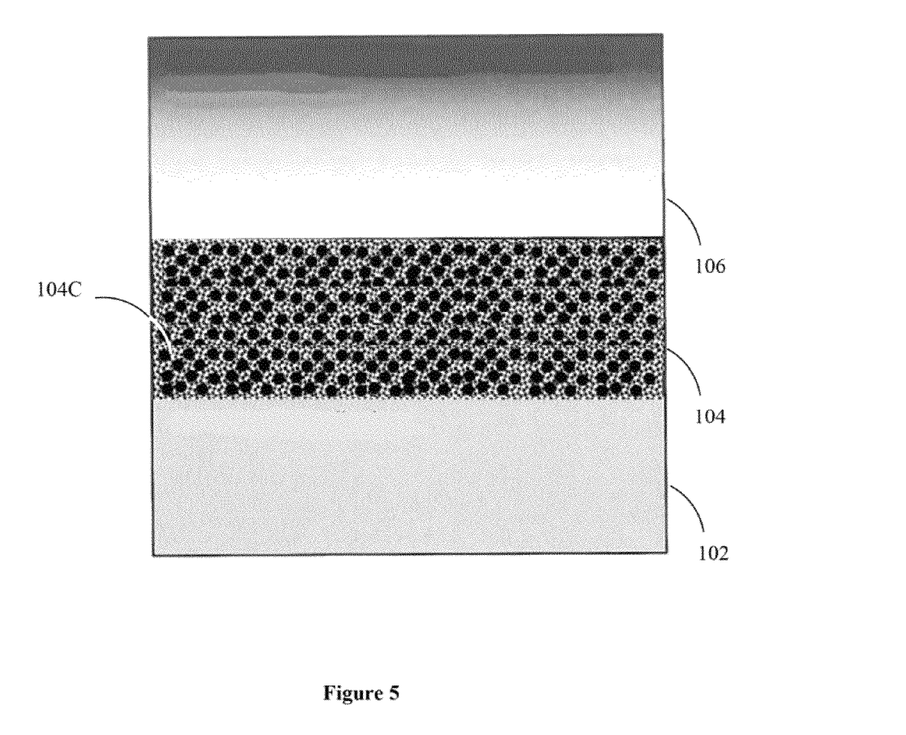
FIG. 5 is a schematic cross-section view of a surgical implant in accordance with an exemplary embodiment of the present invention having the tantalum interlayer comprising nanocomposite tantalum carbide and tantalum dispersed in tantalum.
Figure 6A:
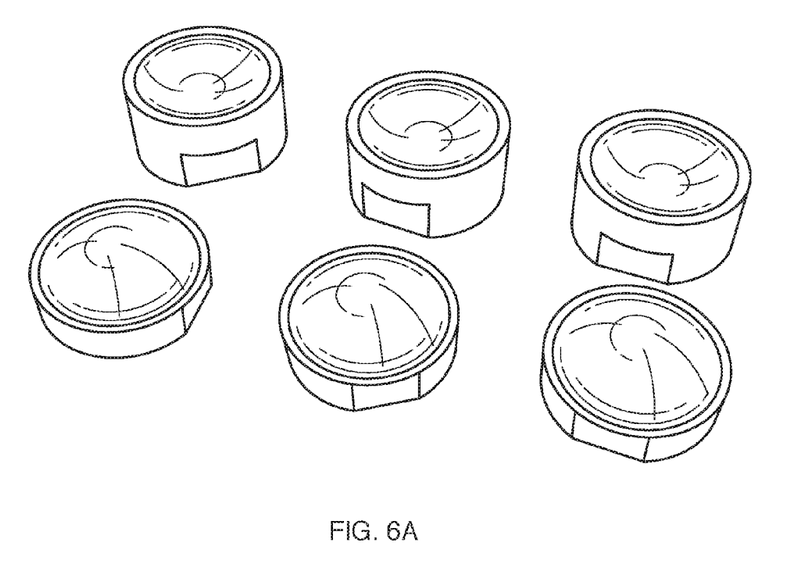
FIG. 6A is an image showing a top perspective view of a cervical disc prosthesis DLC coated in accordance with an exemplary embodiment of the present invention.
Figure 6B:
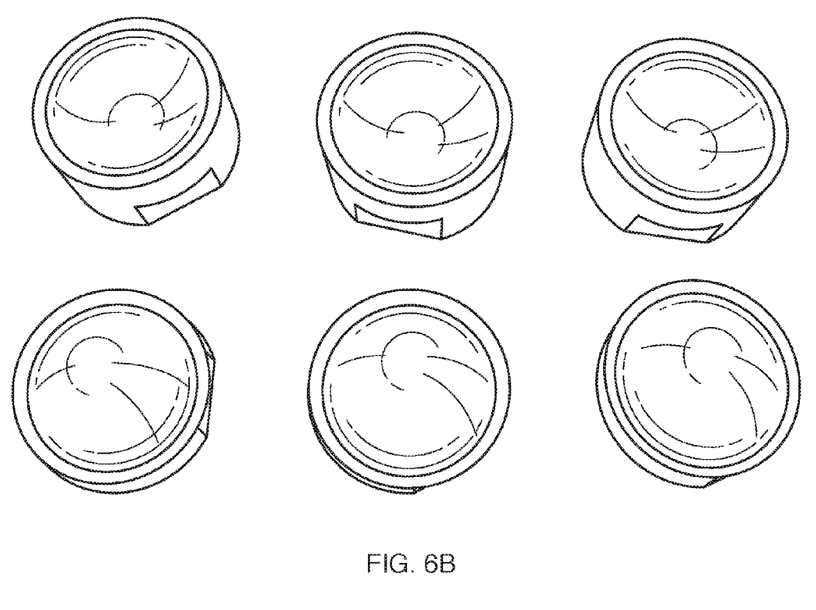
FIG. 6B is another image showing a top perspective view of a cervical disc prosthesis shown in FIG. 6A.

Referring to FIG. 3, in one embodiment, tantalum interlayer 104 comprises nanocomposite tantalum with a tantalum compound, such as a carbide, as a sublayer 104B. In one embodiment, sublayer 104B comprises an element or compound to promote α-tantalum growth. In one such embodiment, the element independently includes titanium, niobium or tungsten. In another such embodiment, the compound independently includes titanium compound, niobium compound or tungsten compound. In one embodiment, tantalum interlayer 104 comprises tantalum as a sublayer 104A and nanocomposite tantalum and a tantalum compound, for example, tantalum carbide, as a sublayer 104. As shown in FIG. 5, in one embodiment, tantalum interlayer 104 is entirely comprised of nanocomposite tantalum and a tantalum compound (see 104C in FIG. 5). In one embodiment, tantalum interlayer 104 comprises a nanocomposite of α-tantalum and a tantalum compound. In one embodiment, tantalum interlayer 104 comprises at least one tantalum layer, of β-tantalum, α-tantalum and mixtures thereof, and at least one nanocomposite tantalum and tantalum compound layer.

Referring to FIGS. 3 and 5, in one embodiment, tantalum interlayer 104 comprises tantalum compound nanoparticles, such as tantalum carbide. In one embodiment, tantalum interlayer 104 comprises tantalum compound nanoparticles and tantalum, as β-tantalum, α-tantalum and mixtures thereof. In one embodiment, tantalum interlayer 104 comprises β-tantalum, amorphous tantalum and tantalum compound nanoparticles. In one embodiment, tantalum interlayer 104 comprises α-tantalum, amorphous tantalum and tantalum compound nanoparticles. In one embodiment, tantalum interlayer 104 comprises β-tantalum, amorphous tantalum and tantalum compound nanoparticles dispersed in tantalum interlayer 104. In one embodiment, tantalum interlayer 104 comprises α-tantalum, amorphous tantalum and tantalum compound nanoparticles dispersed in tantalum interlayer 104. In one embodiment, tantalum interlayer 104 comprises β-tantalum, α-tantalum, amorphous tantalum and tantalum compound nanoparticles dispersed in tantalum interlayer 104.

Referring to FIGS. 2-5, in one embodiment, tantalum interlayer 104 comprises from about 50 to about 100 atomic percent (or at. %) α-tantalum. In one embodiment, tantalum interlayer 104 comprises from about 50 to about 100 atomic percent (or at. %) amorphous tantalum. In one embodiment, tantalum interlayer 104 comprises from about 70 to about 99 atomic percent (or at. %) tantalum compound nanoparticles. In one embodiment, tantalum interlayer 104 comprises from about 10 to about 30 atomic percent (or at. %) α-tantalum; from about 10 to about 30 atomic percent (or at. %) amorphous tantalum; and from about 50 to about 99 atomic percent (or at. %) tantalum compound nanoparticles.

In some embodiments, tantalum interlayer 104 comprises nanocomposite tantalum including a tantalum-carbide composition. In one embodiment, tantalum interlayer 104 comprises nanocomposite tantalum having from about 5 to about 50 atomic percent (or at. %) tantalum and from about 50 to about 99 atomic percent (or at. %) of tantalum carbide.

Referring to FIGS. 2-5, in some embodiments, tantalum interlayer 104 comprises a phase gradient extending at least partially there through. In one embodiment, tantalum interlayer 104 comprises a tantalum phase gradient. In one embodiment, tantalum interlayer 104 comprises a phase gradient including α-tantalum. In one embodiment, tantalum interlayer 104 comprises a phase gradient including amorphous tantalum. In some embodiments, tantalum interlayer 104 comprises a phase gradient including α-tantalum, wherein the phase gradient extends from metallic substrate 102 side of surgical implant 100 to DLC layer 106 side of surgical implant 100. In some embodiments, tantalum interlayer 104 comprises a phase gradient including amorphous tantalum, wherein the phase gradient extends from metallic substrate 102 side of surgical implant 100 to DLC layer 106 side of surgical implant 100. In some embodiments, tantalum interlayer 104 comprises a crystallinity gradient extending at least partially there through. In one embodiment, tantalum interlayer 104 comprises a tantalum crystallinity gradient. In one embodiment, tantalum interlayer 104 comprises a crystallinity gradient including α-tantalum. In one embodiment, tantalum interlayer 104 comprises a crystallinity gradient from β-tantalum to α-tantalum. In some embodiments, tantalum interlayer 104 comprises a crystallinity gradient including α-tantalum, wherein the crystallinity gradient extends from metallic substrate 102 side of surgical implant 100 to DLC layer 106 side of surgical implant 100.

Referring to FIGS. 2-5, in some embodiments, tantalum interlayer 104 has a thickness ranging from about 1 nm to about 2 µm (or 2000 nm). In one embodiment, tantalum interlayer 104 has a thickness having a value in a range selected from the group consisting of: from about 1 nm to about 10 nm, from about 1 nm to about 20 nm; from about 1 nm to about 40 nm, from about 1 nm to about 60 nm; from about 1 nm to about 100 nm; from about 10 nm to about 100 nm, from about 10 nm to about 300 nm, from about 10 nm to about 500 nm, from about 10 nm to about 700 nm, from about 10 nm to about 1000 nm, from about 10 nm to about 1200 nm, from about 10 nm to about 1400 nm, from about 10 nm to about 1600 nm, from about 10 nm to about 1800 nm, from about 10 nm to about 2000 nm; from about 20 nm to about 100 nm, from about 20 nm to about 300 nm, from about 20 nm to about 500 nm, from about 20 nm to about 700 nm, from about 20 nm to about 1000 nm, from about 20 nm to about 1200 nm, from about 20 nm to about 1400 nm, from about 20 nm to about 1600 nm, from about 20 nm to about 1800 nm, from about 20 nm to about 2000 nm; from about 50 nm to about 100 nm, from about 50 nm to about 300 nm, from about 50 nm to about 500 nm, from about 50 nm to about 700 nm, from about 50 nm to about 1000 nm, from about 50 nm to about 1200 nm, from about 50 nm to about 1400 nm, from about 50 nm to about 1600 nm, from about 50 nm to about 1800 nm, from about 50 nm to about 2000 nm; from about 100 nm to about 200 nm, from about 100 nm to about 300 nm, from about 100 nm to about 400 nm, from about 100 nm to about 500 nm, from about 100 nm to about 600 nm, from about 100 nm to about 700 nm, from about 100 nm to about 800 nm, from about 100 nm to about 900 nm, from about 100 nm to about 1000 nm, from about 100 nm to about 1100 nm, from about 100 nm to about 1200 nm, from about 100 nm to about 1300 nm, from about 100 nm to about 1400 nm, from about 100 nm to about 1500 nm, from about 100 nm to about 1600 nm, from about 100 nm to about 1700 nm, from about 100 nm to about 1800 nm, from about 100 nm to about 1900 nm, from about 200 nm to about 300 nm, from about 300 nm to about 400 nm, from about 400 nm to about 500 nm, from about 500 nm to about 600 nm, from about 200 nm to about 400 nm, from about 300 nm to about 500 nm, from about 400 nm to about 600 nm, from about 500 nm to about 700 nm, from about 200 nm to about 500 nm, from about 300 nm to about 600 nm, from about 400 nm to about 700 nm, from about 500 nm to about 800 nm, from about 200 nm to about 600 nm, from about 300 nm to about 700 nm, from about 400 nm to about 800 nm, from about 500 nm to about 900 nm, from about 200 nm to about 700 nm, from about 300 nm to about 800 nm, from about 400 nm to about 900 nm, from about 500 nm to about 1000 nm, from about 200 nm to about 800 nm, from about 300 nm to about 900 nm, from about 400 nm to about 1000 nm, from about 500 nm to about 1100 nm, from about 200 nm to about 900 nm, from about 300 nm to about 1000 nm, from about 400 nm to about 1100 nm, from about 500 nm to about 1200 nm, from about 200 nm to about 1000 nm, from about 300 nm to about 1100 nm, from about 400 nm to about 1200 nm, from about 500 nm to about 1300 nm, from about 200 nm to about 1100 nm, from about 300 nm to about 1200 nm, from about 400 nm to about 1300 nm, from about 500 nm to about 1400 nm, from about 200 nm to about 1200 nm, from about 300 nm to about 1300 nm, from about 400 nm to about 1400 nm, from about 500 nm to about 1500 nm, from about 200 nm to about 1300 nm, from about 300 nm to about 1400 nm, from about 400 nm to about 1500 nm, from about 500 nm to about 1600 nm, from about 200 nm to about 1400 nm, from about 300 nm to about 1500 nm, from about 400 nm to about 1600 nm, from about 500 nm to about 1700 nm, from about 200 nm to about 1500 nm, from about 300 nm to about 1600 nm, from about 400 nm to about 1700 nm, from about 500 nm to about 1800 nm, from about 200 nm to about 1600 nm, from about 300 nm to about 1700 nm, from about 400 nm to about 1800 nm, from about 500 nm to about 1900 nm, from about 200 nm to about 1700 nm, from about 300 nm to about 1800 nm, from about 400 nm to about 1900 nm, from about 500 nm to about 2000 nm, from about 200 nm to about 1800 nm, from about 300 nm to about 1900 nm, from about 400 nm to about 2000 nm, from about 200 nm to about 1900 nm, from about 300 nm to about 2000 nm, from about 200 nm to about 2000 nm, from about 600 nm to about 700 nm, from about 600 nm to about 800 nm, from about 700 nm to about 800 nm, from about 600 nm to about 900 nm, from about 700 nm to about 900 nm, from about 800 nm to about 900 nm, from about 600 nm to about 1000 nm, from about 700 nm to about 1000 nm, from about 800 nm to about 1000 nm, from about 900 nm to about 1000 nm, from about 1000 nm to about 1100 nm, from about 1100 nm to about 1200 nm, from about 600 nm to about 1100 nm, from about 700 nm to about 1100 nm, from about 800 nm to about 1100 nm, from about 900 nm to about 1100 nm, from about 1000 nm to about 1200 nm, from about 1100 nm to about 1300 nm, from about 600 nm to about 1200 nm, from about 700 nm to about 1200 nm, from about 800 nm to about 1200 nm, from about 900 nm to about 1200 nm, from about 1000 nm to about 1300 nm, from about 1100 nm to about 1400 nm, from about 600 nm to about 1300 nm, from about 700 nm to about 1300 nm, from about 800 nm to about 1300 nm, from about 900 nm to about 1300 nm, from about 1000 nm to about 1400 nm, from about 1100 nm to about 1500 nm, from about 600 nm to about 1400 nm, from about 700 nm to about 1400 nm, from about 800 nm to about 1400 nm, from about 900 nm to about 1400 nm, from about 1000 nm to about 1500 nm, from about 1100 nm to about 1600 nm, from about 600 nm to about 1500 nm, from about 700 nm to about 1500 nm, from about 800 nm to about 1500 nm, from about 900 nm to about 1500 nm, from about 1000 nm to about 1600 nm, from about 1100 nm to about 1700 nm, from about 600 nm to about 1600 nm, from about 700 nm to about 1600 nm, from about 800 nm to about 1600 nm, from about 900 nm to about 1600 nm, from about 1000 nm to about 1700 nm, from about 1100 nm to about 1800 nm, from about 600 nm to about 1700 nm, from about 700 nm to about 1700 nm, from about 800 nm to about 1700 nm, from about 900 nm to about 1700 nm, from about 1000 nm to about 1800 nm, from about 1100 nm to about 1900 nm, from about 600 nm to about 1800 nm, from about 700 nm to about 1800 nm, from about 800 nm to about 1800 nm, from about 900 nm to about 1800 nm, from about 1000 nm to about 1900 nm, from about 1100 nm to about 2000 nm, from about 600 nm to about 1900 nm, from about 700 nm to about 1900 nm, from about 800 nm to about 1900 nm, from about 900 nm to about 1900 nm, from about 1000 nm to about 2000 nm, from about nm to about nm, from about 600 nm to about 2000 nm, from about 700 nm to about 2000 nm, from about 800 nm to about 2000 nm, and from about 900 nm to about 2000 nm.

Elemental carbon exists in a number of different forms called allotropes. The most common carbon allotrope is graphite (α-graphite). Diamond is a second allotrope of carbon but is much less common than graphite. Most graphite is α-graphite and it possesses a layer structure in which each carbon atom is directly bound to three other carbon atoms. The bonding between the carbon atoms in each layer structure is described as being three-fold coordinated with trigonal planar coordination geometry reflecting $sp^2$ hybridization of atomic orbitals. In contrast, diamond possesses a structure in which each carbon four-fold coordinated with tetrahedral symmetry reflecting $sp^3$ hybridization of atomic orbitals. DLC is amorphous carbon with high fraction of diamond-like ($sp^3$) bonds between carbon atoms. Reportedly DLC films comprise a combination of four-fold coordinated $sp^3$ sites, as in diamond, and three-fold coordinated $sp^2$ sites, as in graphite.

Referring to FIGS. 2-5, in one embodiment, surgical implant 100 includes at least one DLC layer 106 disposed adjacent tantalum interlayer 104. In one embodiment, DLC layer 106 can be synthesized by any suitable techniques including reactive magnetron sputtering, by physical vapor deposition ("PVD"), chemical vapor deposition ("CVD"), plasma chemical vapor deposition ("PCVD"), plasma-enhanced chemical vapor deposition (PECVD), filtered cathodic vacuum arc, laser ablation, plasma beam source, and dense plasma focusing (DPF). In one embodiment, different deposition methods are used to fabricate DLC layer 106 with preferred tribiological properties. In one embodiment, DLC layer 106 comprises amorphous carbon or amorphous diamond (i-C, tetrahedral amorphous carbon ta-C). In one embodiment, DLC layer 106 comprises hydrogenated amorphous carbon (a-C:H). In one embodiment, DLC layer 106 further including a material comprising an element other than carbon. In one embodiment, DLC layer 106 further including a material comprising an element selected from the group consisting of silicon (Si), nitrogen (N), a metal (Me), fluorine (F). Typically, a DLC film doped with Si, N, metal atoms, and F would be notated as a-Si—C:H, a-C:H—N, a-Me-C:H and a-C:H—F, respectively.

In some embodiments, DLC layer 106 has a hardness value and an elastic modulus value. Referring to FIGS. 2, 3, and 5, in one embodiment, DLC layer 106 has a hardness value having a gradient extending at least partially through DLC layer 106. In one embodiment, DLC layer 106 has a hardness value having a gradient increasing away from tantalum interlayer 104 side. In one embodiment, DLC layer 106 has an elastic modulus value having a gradient increasing away from tantalum interlayer 104 side. In one embodiment, DLC layer 106 has hardness value gradient that increases from about 12 GPa to about 22 GPa. In one embodiment, DLC layer 106 has an elastic modulus value gradient that increases: from about 120 GPa to about 220 GPa; from about 100 GPa to about 200 GPa; from about 50 GPa to about 100 GPa.

Figure 4:
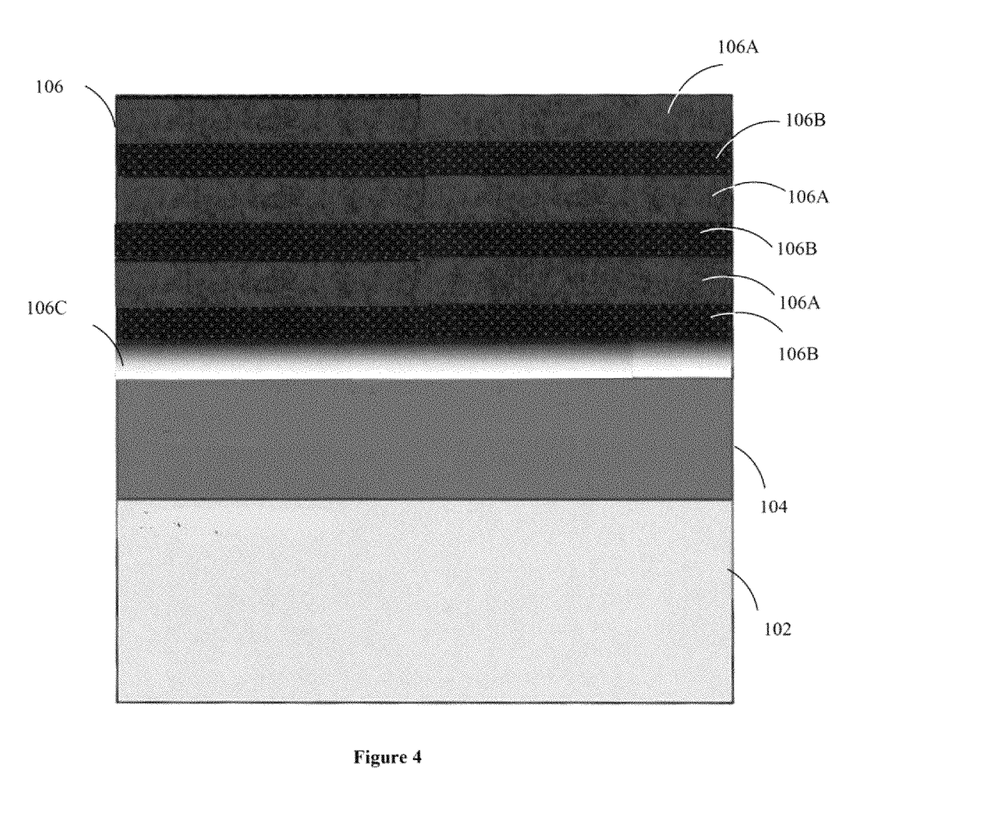
FIG. 4 is a schematic cross-section view of a surgical implant having a coating comprising alternating DLC and metal-doped DLC layers.

Referring to FIG. 4, in some embodiments, at least one DLC layer 106 comprises a plurality of alternating sub-layers comprising a DLC sub-layer 106A and a metal doped DLC sub-layer 106B. In one embodiment, DLC layer 106 comprises a plurality of alternating sub-layers comprising a DLC sub-layer 106A and metal doped DLC sub-layer 106B, wherein metal doped DLC sub-layer 106B is doped with titanium. In one embodiment, at least one DLC layer 106 has graded hardness across at least a portion of it. In one embodiment, the at least one DLC layer 106 has graded hardness tantalum from interlayer 104 side (see 106C in FIG. 4).

Any specific examples of surgical implants described herein should not be construed as limiting the scope of the surgical implants of the present invention, but rather as an exemplification of preferred embodiments thereof. Surgical implants that are contemplated herein include prosthetics which are designed to replace damaged or missing body parts. In some embodiments, surgical implant 100 is placed permanently or is removed from the patient's body once it is no longer needed. In some embodiments, surgical implant 100 is selected from the group consisting of hip implants, chemotherapy ports and screws. In one embodiment, surgical implant 100 is an articulating bone prosthesis. In one embodiment, surgical implant 100 is selected from the group consisting of a total hip joint prosthesis and a total knee joint prosthesis. In one embodiment, surgical implant 100 is metal-on-metal type joint prosthesis.

Surgical implant 100 advantageously minimizes wear debris and toxicity of wear products in articulated joint prostheses, including metal-on-metal ("MOM") joint prostheses, in which both of the articulating surfaces are metal. The DLC and tantalum interlayer coatings of surgical implant 100 beneficially improve performance of metal-on-metal ("MOM") joint prostheses by providing coated articulating surfaces that are hard (wear resistant), chemically inert (biologically compatible) and have low coefficients of friction. One such coating substance is DLC. The DLC and tantalum interlayer coatings of surgical implant 100 beneficially improve chemical and mechanical wear resistance of the coated articulating implants. The DLC and tantalum interlayer coatings of surgical implant 100 beneficially improve adhesion between the coatings and metallic substrate 102 of surgical implant 100 to prevent or retard delamination of the coatings from metallic substrate 102. Compositional gradients of DLC layer 106 and/or tantalum interlayer 104 beneficially improve adhesion between DLC layer 106 and/or tantalum interlayer 104 and metallic substrate 102 and minimize or prevent stresses would have otherwise developed in the non-graded DLC layer 106 and/or non-graded tantalum interlayer 104 either due to lattice mismatch (intrinsic stresses) or difference in the thermal coefficients of non-graded DLC layer 106 and/or non-graded tantalum interlayer 104 and metallic substrate 102 (thermal stresses). Intrinsic stresses and thermal stresses in combination with stresses arising during articulation are known to cause delamination of coated surgical implants.

In another aspect, the present invention provides a method for manufacturing surgical implants in accordance with the exemplary embodiments of the present invention. In one exemplary embodiment, the method for manufacturing surgical implant 100 comprises: (a) inserting metallic substrate 102 into a vacuum system; (b) cleaning metallic substrate 102; (c) depositing tantalum interlayer 104 onto metallic substrate 102; and (d) depositing DLC layer 106 onto tantalum interlayer 104.

In one embodiment, the cleaning of metallic substrate 102 is performed by ion bombardment of metallic substrate 102 from a gaseous plasma. In one embodiment of the ion bombardment, ion bombardment energy and ion flux (density) are preferably controlled by a radio frequency (RF) power. However, in other embodiments, any other power sources with which a varying or static (DC) electric field can be established can be used. In one embodiment, the ion bombardment is preferably performed in vacuum so that a stable RF plasma can be generated. In one embodiment, RF power is used to control the gaseous plasma and ion bombardment process. In one embodiment, increasing the RF power, increases gaseous plasma potential and direct current (DC) equivalent bias. In one embodiment, increasing the RF power, increases ion density of the gaseous plasma. In one embodiment, decreasing the RF power decreases gaseous plasma potential and DC bias (ion bombardment energy). In one embodiment, decreasing the RF power, decreases ion density of the gaseous plasma. In one embodiment, the working pressure of the gases in the vacuum chamber in which metallic substrate 102 is inserted is used to control the gaseous plasma and ion bombardment process.

In one embodiment, cleaning of metallic substrate 102 comprises applying argon ion ($Ar^+$) bombardment to metallic substrate 102 in vacuum. In one embodiment, $Ar^+$ bombardment of metallic substrate 102 in vacuum is performed at a RF self bias of −600 volts. In one embodiment, $Ar^+$ bombardment of metallic substrate 102 in vacuum is performed at a RF self bias of ranging from about −100 volts to about −2000 volts. In one such embodiment, the RF self bias is changed in stepwise increments ranging from a 5 volt step to a 50 volt step.

In one embodiment, the deposition of tantalum interlayer 104 on metallic substrate 102 comprises applying an electrical bias to the substrate during tantalum deposition from a tantalum source. In one embodiment, the electrical bias is a RF self bias. In one embodiment, the deposition of tantalum interlayer 104 on metallic substrate 102 comprises applying a RF self bias to the substrate during a tantalum magnetron sputtering discharge, wherein the RF self bias ranges from −50 volts to −2000 volts, preferably −100 volts to −400 volts. In one embodiment, deposition of tantalum interlayer 104 on metallic substrate 102 comprises applying a RF self bias to a substrate during a tantalum magnetron sputtering discharge, wherein the RF self bias is changed in a in a stepwise manner. In one embodiment, deposition of tantalum interlayer 104 on metallic substrate 102 comprises applying a RF self bias to a substrate during a tantalum magnetron sputtering discharge, wherein the RF self bias is changed in predetermined increments. In one such embodiment, the predetermined increments range from a 5 volt step to a 50 volt step. In one embodiment, deposition of tantalum interlayer 104 on metallic substrate 102 comprises applying a RF self bias to a substrate during a tantalum magnetron sputtering discharge, wherein the RF self bias is changed in a stepwise manner and in predetermined increments. In one such embodiment, the predetermined increments range from a 5 volt step to a 50 volt step. In one embodiment, deposition of tantalum interlayer 104 on metallic substrate 102 comprises applying a RF self bias to a substrate during a tantalum magnetron sputtering discharge, wherein the RF self bias is changed in increments ranging from a 5 volt step to a 50 volt step.

In one embodiment, the deposition of DLC layer 106 comprises introducing a hydrocarbon having a molecular weight ranging from 92 g/mole to 120 g/mole, at a second RF self bias. In one embodiment, the deposition of DLC layer 106 comprises introducing the hydrocarbon having the molecular weight ranging from 92 g/mole to 120 g/mole, at the second RF self bias, wherein the second RF self bias is changed from −50 volts to −600 volts in a stepwise increment. In one embodiment, the deposition of DLC layer 106 comprises introducing the hydrocarbon having the molecular weight ranging from 92 g/mole to 120 g/mole, at the second RF self bias, wherein the second RF self bias is changed from −50 volts to −600 volts in a stepwise increment, and wherein the stepwise increment ranges from a 5 volt step to a 50 volt step. In one embodiment, the deposition of DLC layer 106 comprises introducing the hydrocarbon having the molecular weight ranging from 92 g/mole to 120 g/mole, at the second RF self bias, wherein the hydrocarbon is independently selected from the group consisting of: toluene, xylene, trimethyl benzene, and combinations thereof.

In one embodiment, the method for manufacturing surgical implants in accordance with the present invention further comprises the step of introducing an acetylene atmosphere at a third RF self bias. In one embodiment, the third RF self bias is changed from −50 volts to −600 volts in a second stepwise increment. In one embodiment, the second stepwise increment ranges from a 5 volt step to a 50 volt step.

In another embodiment, the method for manufacturing surgical implants in accordance with the present invention comprises the following: (a) inserting metallic substrate 102 into a vacuum system; (b) cleaning metallic substrate 102 by Ar$^+$ bombardment at a predetermined RF self bias; (c) depositing tantalum interlayer 104 on the metallic substrate 102 by applying a predetermined RF self bias or range of RF self biases during deposition of tantalum from a tantalum magnetron sputter discharge; (d) depositing DLC layer 106 by introducing an acetylene atmosphere at a predetermined RF self bias or range of RF self biases for a first time period; (e) after the first time period, introducing an organotitanium source into the acetylene atmosphere for a second time period; and (f) repeating steps (d) and (e) up to 100 repetitions, 50 repetitions or 10 repetitions.

In one such embodiment, the method for manufacturing surgical implants comprises inserting metallic substrate 102 into a vacuum system and cleaning metallic substrate 102 by Ar$^+$ bombardment at a RF self bias of −600 volts. In one embodiment, the method for manufacturing surgical implants comprises inserting metallic substrate 102 into a vacuum system and cleaning metallic substrate 102 by Ar$^+$ bombardment at a RF self bias of ranging from about −200 to about −2000.

In another such embodiment, the deposition of tantalum interlayer 104 comprises applying a RF self bias to the substrate being coated by a tantalum magnetron discharge, wherein the RF self bias ranges from −50 volts to −600 volts, preferably −100 volts to −400 volts. In one embodiment, deposition of tantalum interlayer 104 comprises applying a RF self bias to the substrate being coated by a tantalum magnetron discharge, wherein the RF self bias is changed in a stepwise manner. In one embodiment, deposition of tantalum interlayer 104 comprises applying a RF self bias to the substrate being coated by a tantalum magnetron discharge, wherein the RF self bias is changed in predetermined increments. In one embodiment, deposition of tantalum interlayer 104 comprises applying a RF self bias to the substrate being coated by a tantalum magnetron discharge, wherein the RF self bias is changed in 50 volts increments.

In another such embodiment, deposition of DLC layer 106 comprises introducing an acetylene atmosphere at a RF self bias, wherein the RF self bias is changed from −50 volts to −600 volts. In one embodiment, deposition of DLC layer 106 comprises introducing an acetylene atmosphere at a RF self bias, wherein the RF self bias is changed from −50 volts to −600 volts in a stepwise increment for a first time period. In one embodiment, deposition of DLC layer 106 comprises introducing an acetylene atmosphere at a RF self bias, wherein the RF self bias is changed from −50 volts to −600 volts in a stepwise increment for a first time period, wherein the stepwise increment ranges from a 5 volt step to a 50 volt step. In one embodiment, the method for manufacturing surgical implants comprises repeating the steps for the deposition of DLC layer 106 a predetermined number of times. In one embodiment, the method for manufacturing surgical implants comprises repeating the steps for the deposition of DLC layer 106 up to ten repetitions. In one embodiment, deposition of DLC layer 106 further comprises introducing an organotitanium source into the acetylene atmosphere after the first time period for a second time period.

EXAMPLES

Example 1

Coating of a Spinal Disk Prosthesis

This example illustrates the coating of a spinal disk prosthesis in accordance with an embodiment of the present invention. The spinal disk prosthesis is made from TiAl6Nb7 alloy featuring a ball-on-socket design. The coating process employed a hybrid plasma-activated metal-organic vapor deposition/physical vapor deposition (PA-MOCVD/PVD).

Supplies used in this example, included a spinal disk prosthesis made from TiAl6Nb7 alloy featuring a ball-on-socket design was used; a 2-inch DC magnetron (Advanced Energy, Fort Collins, USA) sputtering system; EMAG Emmi-Sonic 60 HC ultrasonic cleaning bath (Naenikon, Switzerland); and a cleaning solution comprising 1:1 ethanol/acetone solvent mixture.

The procedure for coating the spinal disk prosthesis used in the present example included following steps.

Step (a): The spinal disk prosthesis was placed in the ultrasonic cleaning bath in a cleaning solvent comprising 1:1 ethanol/acetone mixture. The spinal disk prosthesis was sonicated in the solvent at a frequency of 45 kHz for 10 minutes.

Step (b): The cleaned spinal disk prosthesis from step (a) was inserted into a vacuum chamber of the 2-inch DC magnetron. The 2-inch DC magnetron was equipped with Ta and Ti dc magnetron cathodes, RF substrate bias, and a mass flow controller array for gaseous and vaporized media (MKS Instruments, Norristown, USA), and pumps (Pfeiffer Vacuum GmbH, Asslar, Germany). The vacuum chamber was pumped down (evacuated) to a pressure less than $1 \times 10^{-5}$ Pa.

Step (c): The Ta magnetron target was sputter cleaned by operating the DC magnetron with 0.5 Pa argon atmosphere and 200 W DC sputtering power for 5 minutes.

Step (d): Surfaces of the spinal disk prosthesis were sputter cleaned by operating the RF power source with a 13.56 MHz RF power, a 2.4 Pa argon atmosphere, and regulated RF self bias of −600V for 60 minutes.

Step (e): Tantalum (Ta) interlayer was deposited on the sputter cleaned spinal disk prosthesis by ignition of the Ta magnetron at a running RF self bias of −300V, Ta magnetron power of 200 W, and deposition rate of 400 nm Ta in 60 minutes.

Step (f): The magnetron discharge was shutdown.

Step (g): DLC deposition from a toluene atmosphere at 1.0 Pa, and operating RF power of −300 V, was applied to the spinal disk prosthesis with a stepwise transition to acetylene (operating pressure of 2.5 Pa; RF self bias of −600V; and total layer thickness of 3 micrometers).

Coated spinal disk prosthesis in accordance with procedure described in this example had a DLC coating that exhibited exceptional mechanical (high hardness), optical (high optical band gap), electrical (high electrical resistivity), chemical (inert) and tribological (low friction and wear coefficient) properties. In one embodiment, the coated spinal disk prosthesis had a DLC coating with a hardness and elastic modulus gradient beginning at 12 GPa and 120 GPa, respectively, at the Ta/DLC interface, and ending with 23 GPa and 230 GPa, respectively, at the surface.

Example 2

Coating of a Hip Joint Prosthesis

This example illustrates the coating of a hip joint prosthesis in accordance with an embodiment of the present invention. The hip joint prosthesis is made from TiAl6Nb7 alloy featuring a ball-on-socket design. The coating process employed a hybrid plasma-activated chemical vapor deposition/physical vapor deposition (PA-CVD/PVD).

Supplies used in this example, included a hip joint prosthesis made from TiAl6Nb7 alloy featuring a ball-on-socket design was used; a 2-inch DC magnetron (Advanced Energy, Fort Collins, USA) sputtering system; EMAG Emmi-Sonic 60 HC ultrasonic cleaning bath (Naenikon, Switzerland); and a cleaning solution comprising 1:1 ethanol/acetone solvent mixture.

The procedure for coating the hip joint prosthesis used in the present example included following steps.

Step (a): The hip joint prosthesis made from TiAl6Nb7 alloy was placed in the ultrasonic cleaning bath in a cleaning solvent comprising 1:1 ethanol/acetone mixture. The hip joint prosthesis was sonicated at a frequency of 45 kHz for 10 minutes.

Step (b): The cleaned hip joint prosthesis from step (a) was inserted into a vacuum chamber of the 2-inch DC magnetron. The 2-inch DC magnetron was equipped with Ta and Ti dc magnetron cathodes, RF substrate bias, and a mass flow controller array for gaseous and vaporized media (MKS Instruments, Norristown, USA), and pumps (Pfeiffer Vacuum GmbH, Asslar, Germany). The vacuum chamber was pumped down (evacuated) to a pressure less than $1 \times 10^{-5}$ Pa.

Step (c): The hip joint prosthesis was sputter cleaned by operating the DC magnetron with 0.5 Pa argon atmosphere and 200 W power for 5 minutes.

Step (d): Surfaces of the sputter cleaned hip joint prosthesis were sputter cleaned by operating the RF power source with a 13.56 MHz RF power, a 2.4 Pa argon atmosphere, and regulated RF self bias of −600V for 90 minutes.

Step (e): Ta interlayer was deposited on the sputter cleaned hip joint prosthesis by ignition of the Ta magnetron at running RF self bias of −300V, Ta magnetron power of 200 W, and deposition rate of 400 nm Ta in 45 minutes.

Step (f): Magnetron discharge was shutdown.

Step (g): DLC deposition was applied to the Ta interlayer coated hip joint prosthesis of Step (e) from an acetylene atmosphere at 2.5 Pa, RF self bias of −600V for 1 minute.

Step (h): A flow of argon carrier gas/Titanium-tetraisopropoxide (TTIP) was introduced into the acetylene discharge at Ar flow rate of 10 standard cubic centimeters per minute (sccm) through TTIP bubbler heated to 80° C., for a duration of 1 minute.

Step (i): Steps (g) and (h) were repeated 10 times and then the coated hip joint prosthesis was taken out of the vacuum chamber.

Coated spinal disk prosthesis in accordance with procedure described in this example had a DLC coating that exhibited exceptional mechanical (high hardness), optical (high optical band gap), electrical (high electrical resistivity), chemical (inert) and tribological (low friction and wear coefficient) properties. In one embodiment, the procedure followed in this experiment produced a hip joint prosthesis with a multilayer coating of DLC/Ti oxide doped DLC, which possesses superior flexibility by virtue of having thinner sub-layers compared with a prosthesis that has only one monolithic DLC layer.

It will be appreciated by those skilled in the art that changes could be made to the exemplary embodiments shown and described above without departing from the broad inventive concept thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and features of the disclosed embodiments may be combined. The words "side", "right", "left", "lower" and "upper" designate directions in the drawings to which reference is made. The words "inwardly" and "outwardly" refer to directions toward and away from, respectively, the geometric center of surgical implant 102. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the method does not rely on the particular order of steps set forth herein, the particular order of the steps should not be construed as limitation on the claims. The claims directed to the method of the present invention should not be limited to the performance of their steps in the order written, and one skilled in the art can readily appreciate that the steps may be varied and still remain within the spirit and scope of the present invention.

We claim:

1. A surgical implant comprising:
   a metallic substrate;
   a tantalum interlayer disposed adjacent to the metallic substrate and comprising α-tantalum and amorphous tantalum;
   at least one diamond like carbon ("DLC") layer disposed adjacent the tantalum interlayer;
   wherein the tantalum interlayer has a phase gradient from β-tantalum to α-tantalum or from amorphous tantalum to α-tantalum between a metallic substrate side and a DLC side;
   wherein the DLC layer has a hardness value and an elastic modulus value; and wherein the hardness value has a gradient increasing away from the tantalum side; and wherein the elastic modulus value has a gradient increasing away from the tantalum side.

2. The surgical implant according to claim 1, wherein the metallic substrate is titanium or a titanium based alloy.

3. The surgical implant according to claim 1, wherein the metallic substrate is a cobalt based alloy.

4. The surgical implant according to claim 1, wherein the metallic substrate is steel.

5. The surgical implant according to claim 1, wherein the tantalum interlayer has a thickness ranging from 1 nm to 2 μm.

6. The surgical implant according to claim 1, wherein the tantalum interlayer further comprises a compound or element to promote alpha-tantalum growth.

7. The surgical implant according to claim 6, wherein the compound is independently selected from the group consisting of: a titanium compound, a niobium compound, a tungsten compound and combinations thereof; and the element is independently selected from the group consisting of: titanium, niobium, tungsten and combinations thereof.

8. The surgical implant according to claim 5, wherein the tantalum interlayer further comprises tantalum compound nanoparticles.

9. The surgical implant according to claim 8, wherein the tantalum interlayer is a nanocomposite of tantalum-carbide and tantalum.

10. The surgical implant according to claim 1, wherein the hardness value gradient increases from 12 GPa to 22 GPa.

11. The surgical implant according to claim 10, wherein the elastic modulus value gradient increases from 120 GPa to 220 GPa.

12. The surgical implant according to claim 1, wherein the at least one DLC comprises a plurality of alternating sub-layers comprising a DLC sub-layer and a metal doped DLC sub-layer.

13. The surgical implant according to claim 12, wherein the metal doped DLC sub-layer is doped with titanium.

14. The surgical implant according to claim 1, wherein the phase gradient extends from the metallic substrate side to the DLC side.

* * * * *